(12) United States Patent
Foster et al.

(10) Patent No.: US 7,238,227 B2
(45) Date of Patent: Jul. 3, 2007

(54) MAGENTA METAL CHELATE DYES AND THEIR USE IN INK-JET PRINTERS

(75) Inventors: Clive Edwin Foster, Manchester (GB); Gavin Wright, Manchester (GB); Kevin Johnson, Preston (GB); Mairi Elizabeth Raggatt, Summertown (GB); Prakash Patel, Manchester (GB)

(73) Assignee: Fujifilm Imaging Colorants Limited, Manchester (GB)

( * ) Notice: Subject to any disclaimer, the term of this patent is extended or adjusted under 35 U.S.C. 154(b) by 0 days.

(21) Appl. No.: 10/547,283

(22) PCT Filed: Feb. 17, 2004

(86) PCT No.: PCT/GB2004/000594

§ 371 (c)(1), (2), (4) Date: Aug. 26, 2005

(87) PCT Pub. No.: WO2004/078859

PCT Pub. Date: Sep. 16, 2004

(65) Prior Publication Data

US 2006/0150861 A1    Jul. 13, 2006

Related U.S. Application Data

(60) Provisional application No. 60/472,405, filed on May 22, 2003.

(30) Foreign Application Priority Data

Mar. 6, 2003    (GB) ................................. 0305089.5

(51) Int. Cl.
*C09D 11/00* (2006.01)
*C09D 11/02* (2006.01)
*C09B 45/00* (2006.01)
*B41J 2/01* (2006.01)

(52) U.S. Cl. ............... 106/31.48; 106/31.5; 106/31.77; 106/31.78; 534/707; 347/100

(58) Field of Classification Search ............. 106/31.48, 106/31.5, 31.77, 31.78; 534/707; 347/100
See application file for complete search history.

(56) References Cited

U.S. PATENT DOCUMENTS

| | | | |
|---|---|---|---|
| 2,892,827 A | 6/1959 | Nickel et al. ................ 260/143 |
| 5,330,542 A * | 7/1994 | Maeda et al. ................... 8/639 |
| 5,980,622 A * | 11/1999 | Byers ....................... 106/31.48 |
| 6,755,903 B2 * | 6/2004 | Yamada et al. .......... 106/31.45 |
| 6,827,770 B2 * | 12/2004 | Chino et al. ............. 106/31.46 |
| 6,969,421 B2 * | 11/2005 | Wright et al. .............. 106/31.5 |
| 6,979,364 B2 * | 12/2005 | Wright et al. .............. 106/31.5 |
| 7,025,815 B2 * | 4/2006 | Shimizu et al. .......... 106/31.46 |
| 7,094,280 B2 * | 8/2006 | Shimizu et al. .......... 106/31.46 |
| 7,097,700 B2 * | 8/2006 | Shimizu .................. 106/31.46 |
| 2005/0274280 A1 * | 12/2005 | Wright et al. .............. 106/31.5 |
| 2006/0152565 A1 * | 7/2006 | Foster et al. ................. 347/100 |
| 2006/0180050 A1 * | 8/2006 | Wright et al. ............ 106/31.46 |

FOREIGN PATENT DOCUMENTS

| | | |
|---|---|---|
| BE | 621712 | 12/1962 |
| BE | 626063 | 12/1962 |
| CH | 468 512 | 2/1969 |
| DE | 1 150 768 | 6/1963 |
| DE | 11 50 768 | 6/1963 |
| DE | 1 154 584 | 9/1963 |
| DE | 11 54 584 | 9/1963 |
| DE | 1 813 919 | 7/1970 |
| DE | 2 037 543 | 2/1972 |
| DE | 30 34 486 A1 | 4/1981 |
| EP | 0 053 037 A2 | 6/1982 |

(Continued)

OTHER PUBLICATIONS

Chemical Abstracts, Abstr. No. 138:57604 and JP 2002/371213 A2, Dec. 26, 2002, see abstract and (for example) compound RN 347417-96-3.

(Continued)

*Primary Examiner*—Helene Klemanski
(74) *Attorney, Agent, or Firm*—Morgan Lewis & Bockius LLP

(57) ABSTRACT

A metal chelate compound of Formula: (1) or a salt thereof: [A—N═N—B] M (1) wherein: A is a 5- or 6-membered heterocyclic ring other than a triazole ring, optionally carrying one or more substituents; B is of the Formula (2a) or (2b). Formula (2a) (2b) wherein: X, Y and W are substituents other than H; M is a metal chelated to A—N═N—B; and n is 0 to 4. Also claimed are compositions and inks containing a compound of Formula (1), a process for ink jet printing using the inks and an inkjet printer cartridge containing the ink

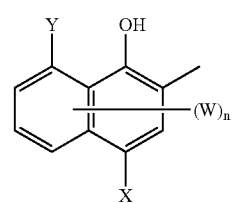

2a

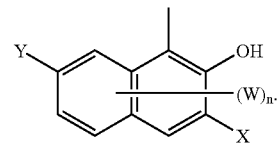

2b

14 Claims, No Drawings

FOREIGN PATENT DOCUMENTS

| | | |
|---|---|---|
| EP | 1 241 232 | 9/2002 |
| EP | 1 241 232 A1 | 9/2002 |
| EP | 1 270 676 | 1/2003 |
| EP | 1 270 676 A1 | 1/2003 |
| GB | 879235 | 10/1961 |
| GB | 974 108 | 11/1964 |
| GB | 974108 | 11/1964 |
| GB | 978721 | 12/1964 |
| GB | 1 428 522 | 3/1976 |
| NL | 6601317 | 8/1966 |
| WO | WO 2004/011561 | 2/2004 |
| WO | WO 2004/011561 A1 | 2/2004 |
| WO | WO 2004/011562 | 2/2004 |
| WO | WO 2004/011562 A1 | 2/2004 |

OTHER PUBLICATIONS

Hirsch et al., "Some New Dyes Based on 3-Amino-1,2,4-Triazole Derivatives",Sbornik Vedeckych Praci/Vysokaskola Chemickotechnologicka Scientific Papers/Univeristy of Chemical Technology, XX, XX, 44:285-290 (1981), no month.

Israilov et al., "Spectrophotometric Study of Triazolyl Azo Compounds and Their Use in Photometric Analysis", Izvestia Akademii Nauk Tadzikskoj SSR, Otdelente Fiziko-Matematiceskih I Geologo-Himiceskih Nauk, Donis, Dusanbe,TJ, 1(79):45-51 (1981), no month available.

Reeves, "Equilibria and Kinetics of Chelation of Nickel(II) by a Solubilised 1-(2-Pyridylazo)-2-naphthol ($\beta$O-PAN) Dye", Inorg. Chem., 25:1473-1478 (1986), no month.

Hirsch B et al.: "Some New Dyes Based on 3-Amino-1,2,4-Triazole Derivatives" Sbornik Vedecych Praci/Vysokaskola Chemickotechnologicka Scientific Papers/University of Chemical Technology, XX,XX, vol. 44, 1981, pp. 285-290, XP009016260, no month available.

Israilov M A et al. : "Spectrophotometric Study of Triazolyl Azo Compounds and Their Use in Photometric Analysis" Izvestia Akademii Nauk Tadzikskih I Geologo-Himiceskih Nauk, Donis, Dusanbe, TJ, vol. 1, No. 79, 1981, pp. 45-51, XP009016505 ISSN: 0002-3485, no month available.

\* cited by examiner

MAGENTA METAL CHELATE DYES AND THEIR USE IN INK-JET PRINTERS

This application claims priority benefit from U.S. Privisional Appln. No. 60/472,405, filed May 22, 2003 and U.K. Appln. No. 0305089.5, filed Mar. 6, 2003.

This invention relates to metal chelate compounds, to inks and to their use in ink jet printing ("IJP").

IJP is a non-impact printing technique in which droplets of ink are ejected through a fine nozzle onto a substrate without bringing the nozzle into contact with the substrate. There are many demanding performance requirements for dyes and inks used in IJP. For example they desirably provide sharp, non-feathered images having good water-fastness, light-fastness and optical density. The inks are often required to dry quickly when applied to a substrate to prevent smudging, but they should not form a crust over the tip of an ink jet nozzle because this will stop the printer from working. The inks should also be stable to storage over time without decomposing or forming a precipitate which could block the fine nozzle.

Colour ink-jet printers typically use four inks of differing hues: magenta, yellow, cyan, and black. Colours other than these may be obtained using differing combinations of these inks. Thus, for optimum print quality, the colorants used must be able to form an ink with a specific precise hue. This can be achieved by mixing colourants but is advantageously achieved by used a single colourant with the exact hue required.

Furthermore, the resultant images desirably do not fade rapidly on exposure to light or common oxidising gases such as ozone.

WO 01/48090 relates to metal chelate compounds which comprise a naphthol component and certain heterocyclic groups. WO 01/48090 does not disclose such compounds specifically substituted at the 3- and 7-positions or at the 4- and 8-positions on the naphthylene ring. Furthermore, WO 01/48090 does not disclose the fact that such substituted compounds have superior properties for use in ink jet printing applications.

According to the present invention there is provided a metal chelate compound of Formula (1) or a salt thereof:

[A—N=N—B]M      Formula (1)

wherein:

A is a 5- or 6-membered heterocyclic ring other than a triazole ring, optionally carrying one or more substituents;

B is of the Formula (2a) or (2b):

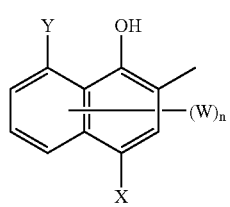

Formula (2a)

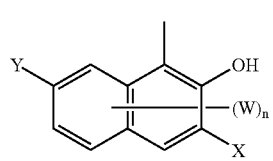

Formula (2b)

wherein:

X, Y and W are substituents other than H;

M is a metal chelated to A—N=N—B; and n is 0 to 4.

A is preferably of the Formula (3):

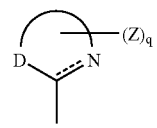

Formula (3)

wherein:

q is 0, 1, 2 or 3;

D is one or more C, N, S or O required for forming a 5- or 6-membered heterocyclic ring other than a triazole ring; and each Z independently is $CF_3$, —OH, —Br, —Cl, —F, —CN, —$NO_2$, phosphoric acid, sulpho, optionally substituted phosphoramide, optionally substituted alkyl, optionally substituted alkenyl, optionally substituted alkynyl, optionally substituted aryl, optionally substituted aralkyl, —$SR^1$, —$SO_2R^1$, —$SO_2NR^2R^3$, —$SOR^1$, —$OR^1$, —$C(O)R^1$, —$C(O)OR^1$, —$C(O)NR^2R^3$, —$NR^2R^3$ or —$NHCOR^1$, wherein $R^1$, $R^2$ and $R^3$ are each independently H, optionally substituted alkyl, optionally substituted alkenyl, optionally substituted alkynyl, optionally substituted aryl or optionally substituted aralkyl; or $R^2$ and $R^3$ together with the nitrogen to which they are attached form an optionally substituted 5- or 6-membered ring.

Preferably A is a pyrazole, imidazole, oxazole, isoxazole, thiazole, isothiazole, pyrimidine, pyridine, pyrazine, pyrimidazine, tetrazole, 1,3,4-thiadiazole, 1,2,4-thiadiazole, pyrazole, 1,3,4-oxadiazole, 1,2,4-oxadiazole, pyrrole, 1,2,4-triazine, 1,3,5-triazine, pyridazine, benzselenazole, benzisoxazole, indazole, indole, benzothiazole, benzoxazole or benzimidazole group, each of which is optionally substituted by Z.

It is especially preferred that A is an optionally substituted imidazole, pyrazole or pyridine group wherein the optional substituents are preferably one or more of the groups described for Z above.

When Z is optionally substituted phosphoramide the phosphoramide is preferably unsubstituted or substituted by optionally substituted alkyl, optionally substituted aryl or optionally substituted aralkyl. Preferred substituents include, for example, methyl, ethyl, n-propyl, iso-propyl, hydroxyethyl, optionally substituted phenyl or optionally substituted benzyl.

When Z is optionally substituted alkyl it is preferably optionally substituted $C_{1-4}$-alkyl, more preferably $C_{1-4}$-alkyl optionally substituted by halo, hydroxy, carboxy, sulpho or cyano. Examples include methyl, ethyl, n-propyl, iso-propyl, trifluoromethyl, hydroxyethyl, cyanoethyl, sulphopropyl and carboxyethyl. When Z is optionally substituted alkyl it is especially preferably methyl, ethyl or trifluoromethyl.

When Z is optionally substituted alkenyl, it is preferably optionally substituted $C_2$-$C_4$ alkenyl.

When Z is optionally substituted alkynyl, it is preferably optionally substituted $C_2$-$C_6$ alkynyl.

When Z is optionally substituted aryl, it is preferably optionally substituted phenyl, optionally substituted naphthyl or optionally substituted heteroaryl, especially optionally substituted phenyl or optionally substituted heteroaryl.

Preferred optional substituents on Z when Z is optionally substituted aryl are selected from sulpho, carboxy, nitro, cyano, halo (preferably chloro), alkoxy (preferably $C_{1-6}$-alkoxy), alkyl (preferably $C_{1-6}$-alkyl, optionally substituted by halogen (preferably fluoro)), hydroxy, carboxy, phosphoric acid and sulpho. When Z is optionally substituted aryl it is especially substituted by $C_{1-4}$-alkyl, carboxy, phosphoric acid, halogen (preferably fluoro), hydroxy and sulpho.

When Z is optionally substituted aralkyl, it is preferably optionally substituted benzyl.

However, Z is most preferably, independently, —SH, carboxy, cyano, halo (preferably chloro or fluoro), alkyl (preferably $C_{1-4}$-alkyl) optionally substituted by hydroxy, carboxy, halo (preferably fluoro) or cyano. It is especially preferred that Z is, independently, a $C_{1-4}$-alkyl, carboxy or cyano group.

$R^1$, $R^2$ and $R^3$ are preferably each independently H, optionally substituted $C_{1-4}$-alkyl or optionally substituted aryl, more preferably H, $C_{1-4}$-alkyl optionally substituted by hydroxy, carboxy, sulpho or cyano or phenyl optionally substituted by hydroxy, carboxy, sulpho, nitro, trifluoromethyl or cyano. Examples of groups represented by $R^1$, $R^2$ and $R^3$ include methyl, ethyl, n-propyl, iso-propyl, hydroxyethyl, cyanoethyl, sulphopropyl, carboxyethyl or carboxyphenyl. It is especially preferred however that $R^1$, $R^2$ and $R^3$ are H, optionally substituted $C_{1-4}$-alkyl (for example, trifluoromethyl, hydroxyethyl or cyanoethyl), or optionally substituted aryl (for example phenyl optionally substituted by carboxy); or $R^2$ and $R^3$ together with the nitrogen to which they are attached form a 5- or 6-membered ring (preferably a morpholine, piperidine or piperazine ring).

It is preferred that when A is a 5-membered heterocyclic ring it is un-substituted or carries one or more substituents selected from $C_{1-4}$-alkyl, cyano and carboxy. It is preferred that when A is a 6-membered heterocyclic ring it is un-substituted or carries one or more groups selected from $C_{1-4}$-alkyl, $C_{1-4}$-alkoxy, cyano and carboxy.

X, Y and W are preferably each independently selected from —OH, —Br, —Cl, —F, —CF$_3$, —CN, —NO$_2$, phosphonic acid, sulpho, optionally substituted phosphoramide, optionally substituted alkyl, optionally substituted alkenyl, optionally substituted alkynyl, optionally substituted aryl, optionally substituted aralkyl, —SR$^1$, —SO$_2$R$^1$, —SO$_2$NR$^2$R$^3$, —SOR$^1$, —OR$^1$, —C(O)R$^1$, —C(O)OR$^1$, —C(O)NR$^2$R$^3$, —NR$^2$R$^3$ and —NHCOR$^1$, wherein $R^1$, $R^2$ and $R^3$ are as described above.

When X, Y or W is optionally substituted alkyl it is preferably optionally substituted $C_{1-4}$-alkyl, more preferably $C_{1-4}$-alkyl optionally substituted by halogen, hydroxy, carboxy, sulpho or cyano. Examples include ethyl, n-propyl, iso-propyl, hydroxyethyl, cyanoethyl, sulpho, propyl and carboxyethyl. When X, Y and W is optionally substituted $C_{1-4}$-alkyl it is especially preferred that it is unsubstituted or substituted by cyano or halogen (preferably fluoro).

When X, Y or W is optionally substituted alkenyl, it is preferably optionally substituted $C_2$-$C_4$ alkenyl.

When X, Y or W is optionally substituted alkynyl, it is preferably optionally substituted $C_2$-$C_6$ alkynyl.

When X, Y or W is optionally substituted aryl, it is preferably optionally substituted phenyl or optionally substituted naphthyl. It is especially preferred that when X, Y or W is optionally substituted aryl it is optionally substituted phenyl.

Preferred optional substituents on X, Y and W when X, Y and W is optionally substituted aryl include: sulpho, carboxy, halogen, alkoxy (preferably $C_{1-6}$-alkoxy) or alkyl (preferably $C_{1-6}$-alkyl) optionally substituted by halogen, nitro, cyano, hydroxy, carboxy, phosphoric acid or sulpho.

When X, Y or W is optionally substituted aralkyl, it is preferably optionally substituted by benzyl.

When X, Y or W is an optionally substituted sulphonamide group it is preferably of the Formula SO$_2$NR$^2$R$^3$, wherein $R^2$ and $R^3$ are as described above. It is preferred that when X, Y or W is of Formula SO$_2$NR$^2$R$^3$, $R^2$ and $R^3$ are each independently H or optionally substituted aryl, most preferably H, optionally substituted phenyl or optionally substituted naphthyl. Especially preferred optional substituents on $R^2$, or $R^3$ when $R^2$ or $R^3$ are optionally substituted aryl include $C_{1-4}$-alkyl, carboxy, phosphoric acid or sulpho. It is most especially preferred that $R^2$ and $R^3$ are each independently H or optionally substituted aryl with the aryl group optionally carrying a carboxy group.

Preferably X, Y and W are each independently selected from sulpho, sulphonamido, carboxy, halogen, nitro and cyano groups, more preferably X, Y and W are sulpho groups.

Preferably q is 1, 2 or 3 more preferably 1 or 2.

M preferably is or comprises one or more of the following metals: nickel, chromium, cobalt, copper, zinc, iron or manganese. It is particularly preferred that M is nickel. Most preferably A—N=N—B is able to chelate to M in the ratio 1:1, 2:1 or 2:2, 2:3 respectively, especially in the ratio 1:1 or 2:1 respectively.

When there is more than one ligand of formula A—N=N—B in the metal chelate compound of Formula (1) then the ligands of formula A—N=N—B may be the same or different but preferably they are the same.

The metal chelate compound of Formula (1) may also comprise 1 or more additional ligands. These ligands may be coloured or colourless and when there is more than 1 they may be the same or different.

Preferably n is 0, 1, 2 or 3, more preferably 1, 2 or 3, especially 1 or 2.

Preferably the compound of Formula (1) is a metal chelate compound of Formula (4a) or (4b) or a salt thereof:

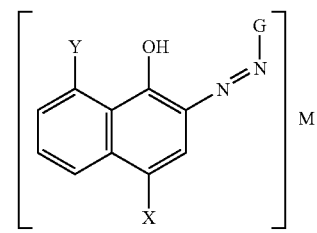

Formula (4a)

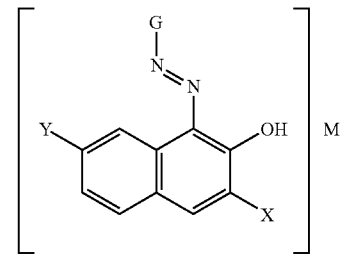

Formula (4b)

wherein

G is an optionally substituted imidazole, pyrazole or pyridine group; and

M is nickel chelated to the group shown in square brackets; and

X and Y are selected from sulpho, sulphonamido, carboxy, halogen, nitro and cyano groups.

In the compounds of Formula (4a) and (4b) the optional substituents which may be present on G are independently as described above for Z, especially cyano, $C_{1-4}$-alkyl, carboxy and sulpho.

It is especially preferred that the compounds of Formula (1) are magenta in colour.

The compounds of the invention exhibit particularly good ozone fastness, optical density and light fastness, making them valuable colorants for photorealistic and other ink jet printing applications.

The compounds of Formula (1) also have good solublility and operability in ink jet printers with a low tendency to crust over or block nozzles when inks containing the compounds are used in an ink jet printer.

Compounds of Formula (1) are preferably free from fibre reactive groups because no such groups are required. Also fibre reactive groups tend to hydrolyse in ink on long term storage which can lead to stability problems. The term fibre reactive group is well known in the art and is described for example in EP 0356014 A1. Fibre reactive groups are capable, under suitable conditions, of reacting with the hydroxyl groups present in cellulosic fibres or with the amino groups present in natural fibres to form a covalent linkage between the fibre and the dye. As examples of fibre reactive groups which are preferably absent from the compounds of Formula (1) there may be mentioned aliphatic sulphonyl groups which contain a sulphate ester group in the beta-position to the sulphur atom, e.g. beta-sulphato-ethylsulphonyl groups, alpha, beta-unsaturated acyl radicals of aliphatic carboxylic acids, for example acrylic acid, alpha-chloro-acrylic acid, alpha-bromoacrylic acid, propiolic acid, maleic acid and mono- and dichloro maleic; also the acyl radicals of acids which contain a substituent which reacts with cellulose in the presence of an alkali, e.g. the radical of a halogenated aliphatic acid such as chloroacetic acid, beta-chloro and beta-bromopropionic acids and alpha, beta-dichloro- and dibromopropionic acids or radicals of vinylsulphonyl- or beta-chloroethylsulphonyl- or beta-sulphatoethylsulphonyl-endo-methylene cyclohexane carboxylic acids. Other examples of cellulose reactive groups are tetrafluorocyclobutyl carbonyl, trifluoro-cyclobutenyl carbonyl, tetrafluorocyclobutylethenyl carbonyl, trifluoro-cyclobutenylethenyl carbonyl; activated halogenated 1,3-dicyanobenzene radicals; and heterocyclic radicals which contain 1, 2 or 3 nitrogen atoms in the heterocyclic ring and at least one cellulose reactive substituent on a carbon atom of the ring.

The compounds described herein may exist in tautomeric forms other than those shown in this specification. These tautomers are also included within the scope of the present inventions.

The metal chelate compounds of Formula (1) may also exist in different geometries eg octahedral. These different geometric forms are also included in the scope of the present invention.

The compounds of Formula (1) may be in the free acid or salt form. Preferred salts are water-soluble, for example alkali metal salts, (especially lithium, sodium, potassium); ammonium, substituted ammonium and mixed salts thereof. Preferred metal salts are those with sodium, lithium, ammonium and substituted alkyl ammonium salts.

Preferred ammonium and substituted alkyl ammonium salts have cations of the formula $^+NV_4$ wherein each V independently is H or optionally substituted alkyl, or two groups represented by V are H or optionally substituted alkyl and the remaining two groups represented by V, together with the N atom to which they are attached, form a 5- or 6-membered ring (preferably a morpholinyl, pyridinyl or piperidinyl ring).

Preferably each V independently is H or $C_{1-4}$-alkyl, more preferably H, $CH_3$ or $CH_2CH_3$, especially H.

Examples of cations include $^+NH_4$, morpholinium, piperidinium, pyridinium, $(CH_3)_3N^+H$, $(CH_3)_2N^+H_2$, $H_2N^+(CH_3)(CH_2CH_3)$, $CH_3N^+H_3$, $CH_3CH_2N^+H_3$, $H_2N^+(CH_2CH_3)_2$, $CH_3CH_2CH_2N^+H_3$, $(CH_3)_2CHN^+H_3$, $N^+(CH_3)_4$, $N^+(CH_2CH_3)_4$, N-meyhyl pyridinium, N,N-dimethyl piperidinium and N,N-dimethyl morpholinium.

It is especially preferred that the compound of Formula (1) is in the form of a sodium, lithium, potassium, ammonium or substituted ammonium salt, because we have found that these salts provide prints which exhibit a high lightfastness when incorporated into an ink jet printing ink.

The compounds of Formula (1) may be converted into a salt using known techniques. For example, an alkali metal salt of a compound may be converted into a salt with ammonia or an amine by dissolving an alkali metal salt of the dye in water and passing the solution through a column of a suitably modified ion exchange resin.

The compounds of Formula (1) may be prepared using conventional techniques for the preparation of metal chelate compounds. For example, a suitable method comprises mixing together a metal salt and a compound of Formula A—N═N—B in solution, wherein A and B are as hereinbefore defined.

The product of the above process may be converted to a salt by conventional techniques as hereinbefore described. Alternatively, the product may be isolated in its free acid form by acidifying the reaction mixture, preferably using a mineral acid, for example hydrochloric acid and when the product precipitates as a solid it may be separated from the mixture by filtration. Unwanted anions may be and preferably are removed from the product of the above process by dialysis, reverse osmosis, ultra filtration or a combination thereof. Alternatively, the product solution is subjected to the above purification directly without isolation of the product.

The compounds of Formula A—N═N—B may be prepared by, for example, diazotising a compound of the formula A—$NH_2$ to give a diazonium salt and coupling the resultant diazonium salt with a compound of the Formula H—B, wherein A and B are as hereinbefore defined.

The diazotisation is preferably performed at a temperature below 20° C., more preferably at a temperature in the range 0° C. to 5° C. Preferably the diazotisation is performed in dilute acid, preferably at a pH below 7. Dilute mineral acid, e.g. HCl or $H_2SO_4$ or an organic acid for example acetic acid, phosphoric acid or a mixture thereof are often used to achieve the desired acidic conditions.

The present invention also provides mixtures comprising two or more compounds of the Formula (1) or salts thereof. Furthermore, the compounds of Formula (1) may be mixed with commercially available dyes, especially those listed in the Colour Index International, to adjust the shade or other properties as desired.

According to a second aspect of the present invention there is provided a composition comprising:
(a) one or more compound according to the first aspect of the present invention; and
(b) one or more water-soluble dye(s) other than a compound according to the first aspect of the invention.

The other water-soluble dye is preferably a water-soluble dye, for example a xanthene dye, an azo or bis azo dye.

Preferred other water-soluble dyes include C.I. Acid Red 50, 52, 87, 91, 92, 95, 249 and 289; C.I. Direct Violet 106 and 107; compounds 100 to 107, 200 and 201 described on pages 8 and 9 of WO96/24636; compounds 1 to 24 shown described on columns 4 to 10 in U.S. Pat. No. 5,542,970; compounds 1 to 55 described on pages 7 to 17 of EP-A-682 088; compounds 1 to 14 shown in Example 1 to 6 of EP-A-194,885; compounds 1 to 24 described on pages 8 to 13 of EP-A-717 089; the compounds described in examples 1 to 16 in columns. 5 to 11 of U.S. Pat. No. 5,262,527; and the dyes described in Examples 1 to 21 in WO 94/16021.

Especially preferred water-soluble dyes for use in the composition according to the second aspect of the invention include C.I. Acid Red 52, C.I. Acid Red 289 or a dye of the Formula (5), (6) and (7) and salts thereof:

The dye of Formula (5) may be prepared using the method described in Example 1 of EP 0559310. The dye of the Formula (6) may be prepared using the method described in Example 3 of International Patent Application WO 94/16021. The dye of Formula (7) may be prepared using the method described in Example 1 of International Patent Application WO 96/24636.

The composition according to the second aspect of the present invention preferably comprises:

(a) from 1 to 99, more preferably from 3 to 70 and especially from 5 to 50 parts in total of the compound(s) according to the first aspect of the invention; and (b) from 99 to 1, more preferably from 30 to 97 parts and especially 95 to 50 parts in total of the water-soluble dye(s);

wherein the parts are by weight and the sum of the parts (a)+(b)=100.

Formula (5)

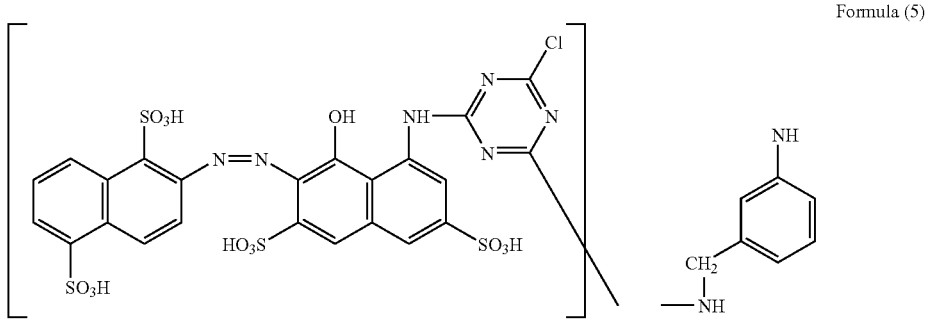

Formula (6)

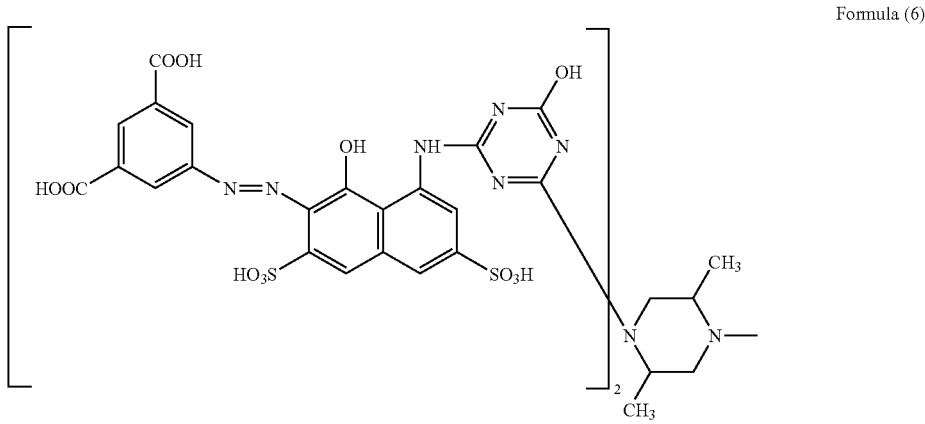

Formula (7)

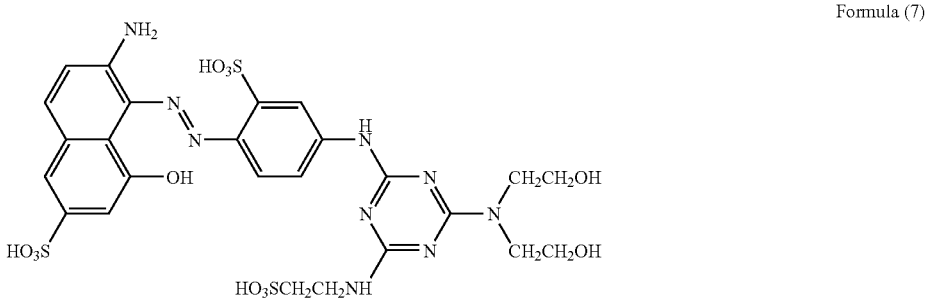

The composition may contain a single dye of Formula (1) or a mixture thereof. Similarly, the composition may contain a single water-soluble dye or a mixture of two or more water-soluble dyes.

The compounds and compositions according to the first and second aspects of the present invention may be, and preferably are, purified to remove undesirable impurities before they are incorporated into inks for ink jet printing. Conventional techniques may be employed for purification, for example ultrafiltration, reverse osmosis and/or dialysis.

According to a third aspect of the present invention there is provided an ink comprising:
(a) a compound according to the first aspect of the present invention, or a composition according to the second aspect of the invention; and
(b) a liquid medium.

The liquid medium preferably comprises:
(i) water;
(ii) a mixture of water and an organic solvent; or
(iii) an organic solvent free from water.

A preferred ink comprises:
(a) a compound of the Formula (1) as defined in the first aspect of the present invention; and
(b) a liquid medium comprising a mixture of water and an organic solvent.

The number of parts by weight of component (a) of the ink is preferably from 0.01 to 30, more preferably 0.1 to 20, especially from 0.5 to 15, and more especially from 1 to 5 parts. The number of parts by weight of component (b) is preferably from 99.99 to 70, more preferably from 99.9 to 80, especially from 99.5 to 85, and more especially from 99 to 95 parts. The number of parts (a)+(b) is 100 and all parts mentioned here are by weight.

Preferably component (a) is completely dissolved in component (b). Preferably component (a) has a solubility in component (b) at 20° C. of at least 10%. This allows the preparation of concentrates which may be used to prepare more dilute inks and reduces the chance of the compound(s) of component (a) of the ink precipitating if evaporation of the liquid medium occurs during storage.

When the liquid medium comprises a mixture of water and an organic solvent, the weight ratio of water to organic solvent is preferably from 99:1 to 1:99, more preferably from 99:1 to 50:50 and especially from 95:5 to 80:20.

It is preferred that the organic solvent present in the mixture of water and organic solvent is a water-miscible organic solvent or a mixture of such solvents. Preferred water-miscible organic solvents include $C_{1-6}$-alkanols, preferably methanol, ethanol, n-propanol, isopropanol, n-butanol, sec-butanol, tert-butanol, n-pentanol, cyclopentanol and cyclohexanol; linear amides, preferably dimethylformamide or dimethylacetamide; ketones and ketone-alcohols, preferably acetone, methyl ether ketone, cyclohexanone and diacetone alcohol; water-miscible ethers, preferably tetrahydrofuran and dioxane; diols, preferably diols having from 2 to 12 carbon atoms, for example pentane-1,5-diol, ethylene glycol, propylene glycol, butylene glycol, pentylene glycol, hexylene glycol and thiodiglycol and oligo- and poly-alkyleneglycols, preferably diethylene glycol, triethylene glycol, polyethylene glycol and polypropylene glycol; triols, preferably glycerol and 1,2,6-hexanetriol; mono-$C_{1-4}$-alkyl ethers of diols, preferably mono-$C_{1-4}$-alkyl ethers of diols having 2 to 12 carbon atoms, especially 2-methoxyethanol, 2-(2-methoxyethoxy)ethanol, 2-(2-ethoxyethoxy)-ethanol, 2-[2-(2-methoxyethoxy)ethoxy] ethanol, 2-[2-(2-ethoxyethoxy) -ethoxy]-ethanol and ethyleneglycol monoallylether; cyclic amides, preferably 2-pyrrolidone, N-methyl-2-pyrrolidone, N-ethyl-2-pyrrolidone, caprolactam and 1,3-dimethylimidazolidone; cyclic esters, preferably caprolactone; sulphoxides, preferably dimethyl sulphoxide and sulpholane. Preferably the liquid medium comprises water and 2 or more, especially from 2 to 8, water-miscible organic solvents.

When the liquid medium comprises an organic solvent free from water, (i.e. less than 1% water by weight) the solvent preferably has a boiling point in the range of from 30° to 200° C., more preferably in the range of from 40° to 150° C. The organic solvent may be water-immiscible, water-miscible or a mixture of such solvents. Preferred water-miscible organic solvents are any of the hereinbefore described water-miscible organic solvents and mixtures thereof. Preferred water-immiscible solvents include, for example, aliphatic hydrocarbons; esters, preferably ethyl acetate; chlorinated hydrocarbons, preferably $CH_2Cl_2$; and ethers, preferably diethyl ether, and mixtures thereof.

When the liquid medium comprises a water-immiscible organic solvent, preferably a polar solvent is included because this enhances solubility of the dye in the liquid medium. Examples of polar solvents include $C_{1-4}$-alcohols. In view of the foregoing preferences it is especially preferred that where the liquid medium is an organic solvent free from water it comprises a ketone (especially methyl ethyl ketone) and/or an alcohol (especially a $C_{1-4}$-alkanol, such as ethanol or propanol).

The organic solvent free from water may be a single organic solvent or a mixture of two or more organic solvents. It is preferred that when the medium is an organic solvent free from water it is a mixture of 2 to 5 different organic solvents. This allows a medium to be selected which gives good control over the drying characteristics and storage stability of the ink.

Ink media comprising an organic solvent free from water are particularly useful where fast drying times are required and particularly when printing onto hydrophobic and non-absorbent substrates, for example plastics, metal and glass.

An especially preferred ink comprises:
(a) from 1 to 10 parts in total of a compound or composition according to the first or second aspect of the invention;
(b) from 2 to 60, more preferably 5 to 40 parts of water-soluble organic solvent; and
(c) from 30 to 97, more preferably 40 to 85 parts water;

wherein all parts are by weight and the sum of the parts (a)+(b)+(c)=100.

When the liquid medium in the ink comprises a mixture of water and an organic solvent; or an organic solvent free from water, component (a) of the ink comprises a compound of the Formula (1), or salt thereof, as hereinbefore defined in relation to the first aspect of the invention.

Preferred low melting solid media have a melting point in the range from 60° C. to 125° C. Suitable low melting point solids include long chain fatty acids or alcohols, preferably those with $C_{18-24}$ chains, and sulphonamides. A compound of Formula (1) may be dissolved in the low melting point solid or may be finely dispersed in it.

The inks according to the present invention may of course also contain further additional components conventionally used in ink jet printing inks, for example viscosity and surface tension modifiers, corrosion inhibitors, biocides, kogation reducing additives, anti-cockle agents to reduce paper curling and surfactants which may be ionic or non-ionic.

The pH of the ink is preferably from 4 to 11, more preferably from 7 to 10.

The inks of the present invention preferably form the magenta ink of a standard magenta, yellow, cyan and black ink set. Typically in such an ink set the yellow ink will contain CI Direct yellow 86, 142 or Pro-Jet™ Fast yellow 2; the cyan ink will contain CI Direct blue 86, 199 or Pro-Jet™ Fast cyan 2; and the black ink will contain CI Direct black 199 or ProJet™ Fast black 2 (Pro-Jet is a trademark of Avecia Limited).

It is preferred that the composition according to the invention is an ink suitable for use in an ink-jet printer. Ink suitable for use in an ink-jet printer is an ink which is able to repeatedly fire through an ink-jet printing head without causing blockage of the fine nozzles.

The inks may be incorporated in an ink-jet printer as a high concentration ink, a low concentration ink or both a high concentration and a low concentration ink. In the latter case this can lead to improvements in the quality of printed images. Thus the present invention also provides a composition where component (a) is present in an amount of 2.5 to 7 parts, more preferably 2.5 to 5 parts (a high concentration ink) or component (a) is present in an amount of 0.5 to 2.4 parts, more preferably 0.5 to 1.5 parts (a low concentration ink).

An ink suitable for use in an inkjet printer preferably has a viscosity of less than 20 cP, more preferably less than 10 cP, especially less than 5 cP, at 25° C.

An ink suitable for use in an ink-jet printer preferably contains less than 500 ppm, more preferably less than 250 ppm, especially less than 100 ppm, more especially less than 10 ppm in total of divalent and trivalent metal ions (other than any divalent and trivalent metal ions bound to a colorant of Formula (1) or any other component of the ink).

Preferably an ink suitable for use in an ink-jet printer has been filtered through a filter having a mean pore size below 10 μm, more preferably below 3 μm, especially below 2 μm, more especially below 1 μm. This filtration removes particulate matter that could otherwise block the fine nozzles found in many ink-jet printers.

Preferably an ink suitable for use in an ink-jet printer contains less than 500 ppm, more preferably less than 250 ppm, especially less than 100 ppm, more especially less than 10 ppm in total of halide ions.

A fourth aspect of the present invention provides a process for printing an image on a substrate comprising applying thereto by means of an ink jet printer an ink containing a compound according to the first aspect of the invention or a composition according to the second aspect of the invention. The ink used in this process is preferably as defined in the third aspect of the present invention.

The ink jet printer preferably applies the ink to the substrate in the form of droplets which are ejected through a small orifice onto the substrate. Preferred ink jet printers are piezoelectric ink jet printers and thermal ink jet printers. In thermal ink jet printers, programmed pulses of heat are applied to the ink in a reservoir by means of a resistor adjacent to the orifice, thereby causing the ink to be ejected in the form of small droplets directed towards the substrate during relative movement between the substrate and the orifice. In piezoelectric ink jet printers the oscillation of a small crystal causes ejection of the ink from the orifice. Alternately the ink can be ejected by an electromechanical actuator connected to a moveable paddle or plunger, for example as described in International Patent Application WO 00/48938 and International Patent Application WO 00/55089.

The substrate is preferably paper, plastic, a textile, metal or glass, more preferably paper, an overhead projector slide or a textile material, especially paper. Preferred papers are plain or treated papers which may have an acid, alkaline or neutral character. Glossy papers are especially preferred. More especially photographic quality paper is preferred Examples of commercially available papers include, HP Premium Coated Paper, HP Photopaper (all available from Hewlett Packard Inc.), Stylus Pro 720 dpi Coated Paper, Epson Photo Quality Glossy Film, Epson Photo Quality Glossy Paper (available from Seiko Epson Corp.), Canon HR 101 High Resolution Paper, Canon GP 201 Glossy Paper, Canon HG 101 High Gloss Film (all available from Canon Inc.), Wiggins Conqueror paper (available from Wiggins Teape Ltd), Xerox Acid Paper and Xerox Alkaline paper (available from Xerox).

A fifth aspect of the present invention provides a substrate, preferably a paper, an overhead projector slide or a textile material, printed with an ink according to the third aspect of the present invention or by means of the process according to the fourth aspect of the present invention.

It is especially preferred that the fifth aspect of the invention is a photographic quality print.

According to a sixth aspect of the present invention there is provided an ink jet printer cartridge comprising a chamber and ink, wherein the ink is present in the chamber and the ink contains a compound or a composition according to the first or second aspect of the present invention. Preferably the ink is as defined in the third aspect of the present invention.

According to a seventh aspect of the present invention there is provided an ink jet printer containing an ink jet printer cartridge, wherein the ink jet printer cartridge is as defined in the sixth aspect of the present invention.

The invention is further illustrated by the following Examples in which all parts and percentages are by weight unless otherwise stated.

EXAMPLE 1

Preparation of the Nickel Chelate Compound (1)

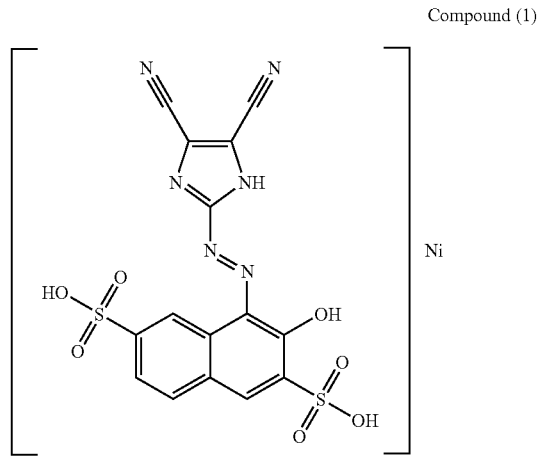

Compound (1)

Compound (1) was Prepared According to the Stages (a) to (c):

Stage (a): Preparation of 3-hydroxynaphthalene-2,6-disulfonic Acid

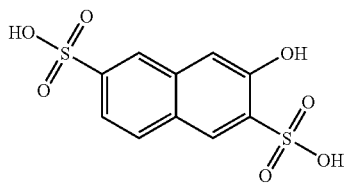

7-Hydroxynaphthalene-2-sulfonic acid (250 g, 1.16 mol) was added in portions to a mixture of concentrated $H_2SO_4$ (950 g) and water (50 g). The mixture was stirred at 110-120° C. for 3 hours, cooled to room temperature, added to a mixture of ice and water (5000 ml) and the product precipitated by the addition of sodium chloride. The resultant slurry was warmed to 90° C. to dissolve the product, stirred for 1 hour at this temperature and then allowed to cool. The product was filtered off and the damp product dissolved in water (3000 ml) at pH 10 by the addition of concentrated sodium hydroxide solution. The solution was then filtered to remove a small amount of insoluble material. The pH of the filtrate was lowered to 7 with concentrated HCl and the product precipitated by the addition sodium chloride. The product was filtered off and dried in a vacuum oven to give 117 g of a cream solid (68% yield).

Stage (b):

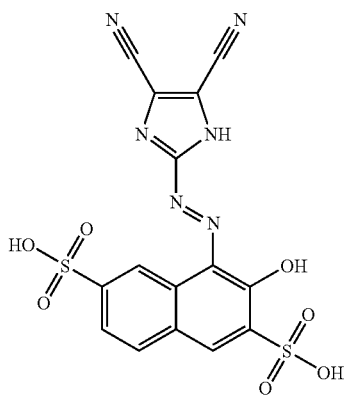

2-Amino-4,5-imidazoledicarbonitrile (3.99 g, 0.03 mol) was suspended in water (100 ml) and dissolved by the addition of 2M NaOH to pH 8. Sodium nitrite (2.27 g, 0.033 mol) was added and the solution stirred until the sodium nitrite had dissolved.

The mixture was then added dropwise to a cooled mix of ice-water (150 g) and concentrated HCl (10 ml) at 0-5° C., the mixture was stirred for 60 minutes at 0-5° C. and then excess nitrous acid was removed by adding sulphamic acid. The diazo suspension was added slowly to a solution of 3-hydroxynaphthalene-2,6-disulfonic acid (13.4 g, 0.03 mol) in water (300 ml) at pH 7-8 (2N NaOH) and cooled below 5° C. The reaction mixture was then stirred at 0-5° C. for one further hour, the product was precipitated by acidification to pH 4 with 2M HCl and collected by filtration. The product was washed with 15% brine solution and then dried in a vacuum desiccator to give 29 g of a dark orange solid (32% yield).

Stage (c): Preparation of Compound (1)

A solution of nickel acetate tetrahydrate (2.5 g, 0.01 mol) in water (20 ml) was added dropwise to the product from stage (b) (14.0 g, 0.01 mol) dissolved in water (100 ml) at pH 7-8 (2N NaOH). The reaction mixture was stirred for 2 hours at 20° C. and dialysed, using SpectraPor membrane tubing (molecular weight cut off 3500), to low conductivity. Compound (1) was obtained by evaporation under reduced pressure to afford a dark solid (5 g).

EXAMPLE 2

Preparation of Compound (2) wherein M is Nickel

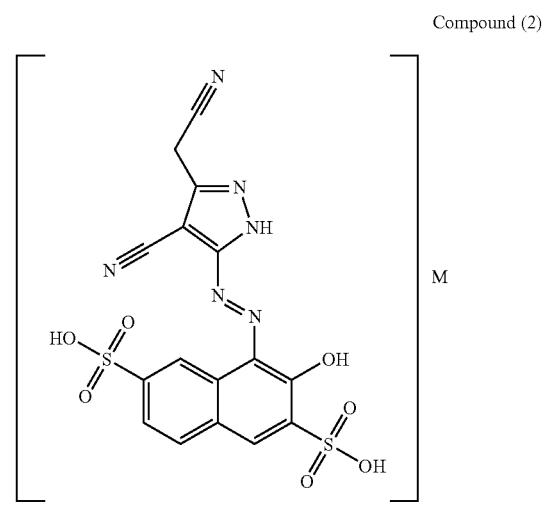

Compound (2)

Compound (2) was prepared using an analogous process to that described in Example (1) except that in stage (b) 5-amino-3-cyanomethyl-1H-pyrazole-4-carbonitrile (4.41 g, 0.03 mol) was used in place of 2-amino-4,5-imidazoledicarbonitrile.

EXAMPLE 3

Preparation of Compound (3) where M is Nickel

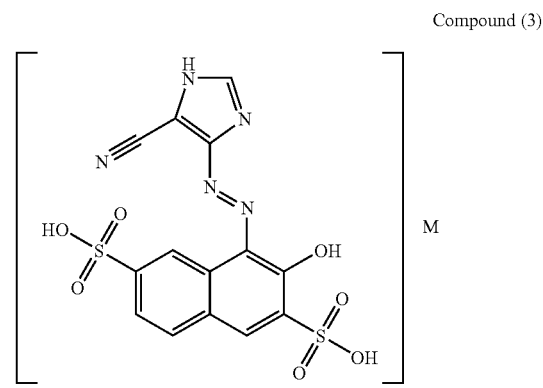

Compound (3)

Compound (3) was prepared using an analogous process to that described in Example (1) except that in stage (b) 5-amino-3H-imidazole-4-carbonitrile (3.24 g, 0.03 mol) was used in place of 2-amino-4,5-imidazoledicarbonitrile

EXAMPLE 4

Preparation of Compound (4) wherein M is Nickel

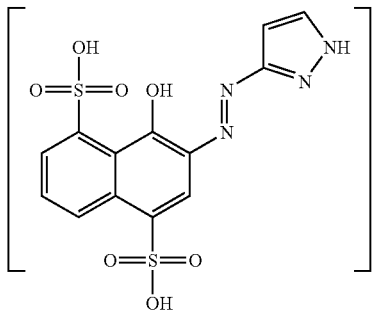

Compound (4)

Compound (4) was Prepared According to the Stages (a) to (d):

Stage (a):

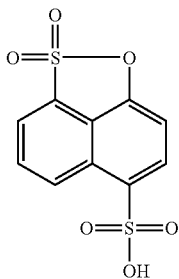

1,8-Naphthosultone (25.0 g, 0.119 mol) was added in portions to concentrated sulphuric acid (75 ml), the reaction mixture was then stirred for 2 hours at 80° C. and then added to a mixture of ice (70 g) and water (20 ml). Anhydrous sodium sulphate (46 g) was added in portions to the reaction mixture at 30° C., the product was collected by filtration and then dissolved in water (120 ml) at 50° C. The product was precipitated by the addition of sodium chloride (25% w/v), stirred at 40° C. for 1 hour and then collected by filtration. The solid was dried in a vacuum oven to give 30 g of a pink solid (76%).

Stage (b):

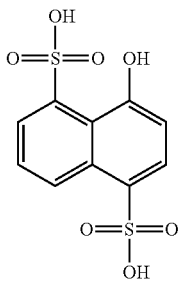

The product from stage (a) (30 g) was dissolved in water (200 ml) at pH 11 by the addition of 2M sodium hydroxide. The solution was stirred at room temperature for 2 hours to complete the hydrolysis and the solution of the product used in the next stage without isolation.

Stage (c):

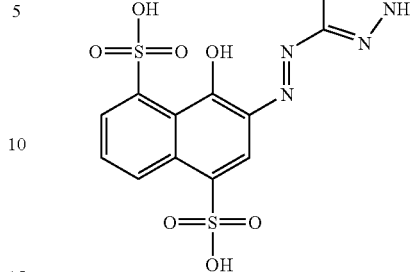

A solution of sodium nitrite (5.45 g, 0.079 mol) in water (20 ml) was added dropwise to a suspension of 3-aminopyrazole (5.60 g, 0.066 mol) in water (100 ml) and concentrated HCl (25 ml) 0-5° C. The mixture was stirred for 30 minutes at 0-5° C. and then excess nitrous acid was removed by adding sulphamic acid. The diazo solution was added slowly to the solution of the product from stage (b) (0.09 mol) in water (300 ml) at pH 9 (2M NaOH) and cooled below 5° C. The reaction mixture was then stirred at 0-5° C. for one further hour, the product was collected by filtration, washed with acetone and dried to give 21 g of a dark red solid (80% pure).

Stage (d): Preparation of Compound (4)

A solution of nickel acetate tetrahydrate (2.52 g, 0.10 mol) in water (50 ml) was added dropwise to the product from stage (a) (5.0 g, 0.01 mol) dissolved in water (100 ml) at pH 8.5 (2N NaOH). The reaction mixture was stirred for 1 hour at 70° C., dialysed using SpectraPor membrane tubing (3500 molecular weight cut off) to low conductivity (<100 μs). Compound (1) was obtained by evaporation under reduced pressure to afford a dark solid (3.6 g).

EXAMPLE 5

Preparation of Compound (5) where M is Nickel

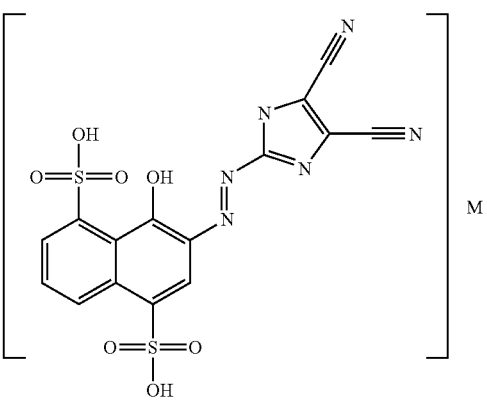

Compound (5)

Compound (5) was prepared using an analogous process to that described in Example (4) except that in stage (c) 2-Amino-4,5-imidazoledicarbonitrile (8.05 g, 0.066 mol) was used in place of 3-aminopyrazole.

Comparative Dye

The Comparative Dye was compound 1-38 from WO 01/48090 and was of Formula:

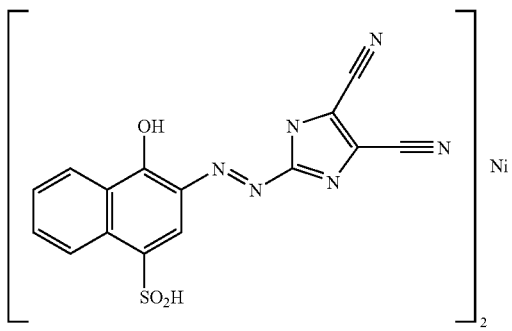

EXAMPLE 6

Inks and Inkjet Printing

Preparation of Inks

The dye described in Example 5 and the Comparative Dys were converted into inks were by dissolving 3.5 parts of each in 96.5 parts of a liquid medium comprising:
5 parts 2-pyrrolidone;
5 parts thiodiglycol;
2 parts Surfynol™ 465 (a non-ionic surfactant available from Air Products Inc.);
88 parts water: and
adjusted to pH 9.5 with ammonium hydroxide.

The inks so prepared were designated as Ink 5 and Comparative Ink.

Ink-Jet Printing

Ink 5 and the Comparative Ink were filtered through 0.45 micron nylon filters and then incorporated into empty ink-jet print cartridges using a syringe.

The inks were then printed using an HP560C printer onto Epson Premium Photopaper™ (SEC PM) to give prints at full strength (100%).

These prints were tested for ozone fastness by exposure to 1 ppm ozone at 40° C., 50% relative humidity for 24 hrs in a Hampden 903 Ozone cabinet. Fastness of the printed ink to ozone was judged by the difference in the optical density before and after exposure to ozone.

Light-fastness of the printed image was assessed by fading the printed image in an Atlas Ci5000 Weatherometer for 100 hours and then measuring the change in the optical density.

Optical density measurements of the prints were performed using a Gretag spectrolino spectrophotometer set to the following parameters:
Measuring Geometry: 0°/45°
Spectral Range: 400-700 nm
Spectral Interval: 20 nm
Illuminant: D65
Observer: 2° (UE 1931)
Density: Ansi A
External Filler: None Fastness to ozone or light is expressed as the percentage change in the optical density of the print, where a lower figure indicates higher fastness. Results are shown below.

TABLE 1

|  | % OD Loss Light-fastness | % OD Loss Ozone-fastness |
| --- | --- | --- |
| Ink 5 | 16 | 0 |
| Comparative Ink | 25 | 6 |

Table 1 shows that the inks of the present invention have an improved light and ozone fastness when compared to similar analogues.

Other Inks

The inks described in Tables A and B may be prepared wherein the Compound described in the first column is the Compound made in the above Examples of the same number. Numbers quoted in the second column onwards refer to the number of parts of the relevant ingredient and all parts are by weight. The inks may be applied to paper by thermal or piezo ink jet printing.

The following abbreviations are used in Tables A and B:
PG=propylene glycol
DEG=diethylene glycol
NMP=N-methylpyrollidone
DMK=dimethylketone
IPA=isopropanol
MEOH=methanol
2P=2-pyrollidone
MIBK=methylisobutyl ketone
P12=propane-1,2-diol
BDL=butane-2,3-diol
CET=cetyl ammonium bromide
PHO=$Na_2HPO_4$ and
TBT=tertiary butanol
TDG=thiodiglycol

TABLE A

| Compound | Dye Content | Water | PG | DEG | NMP | DMK | NaOH | Na Stearate | IPA | MEOH | 2P | MIBK |
| --- | --- | --- | --- | --- | --- | --- | --- | --- | --- | --- | --- | --- |
| 1 | 2.0 | 80 | 5 |  | 6 | 4 |  |  |  |  | 5 |  |
| 2 | 3.0 | 90 |  | 5 | 5 |  | 0.2 |  |  |  |  |  |
| 3 | 10.0 | 85 | 3 |  | 3 | 3 |  |  |  | 5 | 1 |  |
| 4 | 2.1 | 91 |  | 8 |  |  |  |  |  |  |  | 1 |
| 4 | 3.1 | 86 | 5 |  |  |  |  | 0.2 | 4 |  |  | 5 |
| 3 | 1.1 | 81 |  |  | 9 |  | 0.5 | 0.5 |  |  | 9 |  |
| 1 | 2.5 | 60 | 4 | 15 | 3 | 3 |  |  | 6 | 10 | 5 | 4 |
| 2 | 5 | 65 |  | 20 |  |  |  |  |  | 10 |  |  |
| 2 | 2.4 | 75 | 5 | 4 |  | 5 |  |  |  | 6 |  | 5 |

TABLE A-continued

| Compound | Dye Content | Water | PG | DEG | NMP | DMK | NaOH | Na Stearate | IPA | MEOH | 2P | MIBK |
|---|---|---|---|---|---|---|---|---|---|---|---|---|
| 1 | 4.1 | 80 | 3 | 5 | 2 | 10 | | 0.3 | | | | |
| 4 | 3.2 | 65 | | 5 | 4 | 6 | | | 5 | 4 | 6 | 5 |
| 3 | 5.1 | 96 | | | | | | | | 4 | | |
| 2 | 10.8 | 90 | 5 | | | | | | 5 | | | |
| 1 | 10.0 | 80 | 2 | 6 | 2 | 5 | | | 1 | | 4 | |
| 4 | 1.8 | 80 | | 5 | | | | | | | 15 | |
| 2 | 2.6 | 84 | | | 11 | | | | | | 5 | |
| 1 | 3.3 | 80 | 2 | | | 10 | | | | 2 | | 6 |
| 3 | 12.0 | 90 | | | | 7 | 0.3 | | 3 | | | |
| 2 | 5.4 | 69 | 2 | 20 | 2 | 1 | | | | | 3 | 3 |
| 1 | 6.0 | 91 | | | 4 | | | | | | 5 | |

TABLE B

| Compound | Dye Content | Water | PG | DEG | NMP | CET | TBT | TDG | BDL | PHO | 2P | PI2 |
|---|---|---|---|---|---|---|---|---|---|---|---|---|
| 4 | 3.0 | 80 | 15 | | | 0.2 | | | | | 5 | |
| 2 | 9.0 | 90 | | 5 | | | | | | 1.2 | | 5 |
| 3 | 1.5 | 85 | 5 | 5 | | 0.15 | 5.0 | 0.2 | | | | |
| 1 | 2.5 | 90 | | 6 | 4 | | | | | 0.12 | | |
| 4 | 3.1 | 82 | 4 | 8 | | 0.3 | | | | | | 6 |
| 2 | 0.9 | 85 | | 10 | | | | | 5 | 0.2 | | |
| 3 | 8.0 | 90 | | 5 | 5 | | | 0.3 | | | | |
| 1 | 4.0 | 70 | | 10 | 4 | | | | 1 | | 4 | 11 |
| 2 | 2.2 | 75 | 4 | 10 | 3 | | | | 2 | | 6 | |
| 1 | 10.0 | 91 | | | 6 | | | | | | 3 | |
| 3 | 9.0 | 76 | | 9 | 7 | | 3.0 | | | 0.95 | 5 | |
| 2 | 5.0 | 78 | 5 | 11 | | | | | | | 6 | |
| 1 | 5.4 | 86 | | | 7 | | | | | | 7 | |
| 4 | 2.1 | 70 | 5 | 5 | 5 | 0.1 | 0.2 | 0.1 | 5 | 0.1 | 5 | |
| 3 | 2.0 | 90 | | | 10 | | | | | | | |
| 1 | 2 | 88 | | | | | | 10 | | | | |
| 2 | 5 | 78 | | | 5 | | | 12 | | | 5 | |
| 1 | 8 | 70 | 2 | | 8 | | | 15 | | | 5 | |
| 4 | 10 | 80 | | | | | | 8 | | | 12 | |
| 1 | 10 | 80 | | | 10 | | | | | | | |

The invention claimed is:

1. A metal chelate compound of Formula (1) or a salt thereof:

[A—N=N—B]M  Formula (1)

wherein:

A is a 5- or 6-membered heterocyclic ring other than a triazole ring, optionally carrying one or more substituents;

B is of the Formula (2a) or (2b):

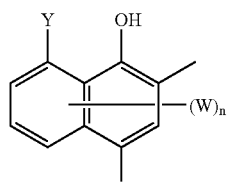

Formula (2a)

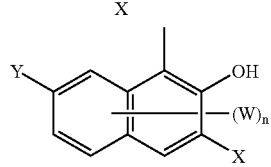

Formula (2b)

wherein:

X, Y and W are substituents other than H;
M is a metal chelated to A—N=N—B; and
n is 0 to 4.

2. A compound according to claim 1 wherein A is of the Formula (3):

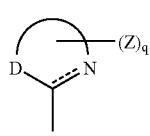

Formula (3)

wherein:

q is 0, 1, 2 or 3;

D is one or more C, N, S or O required for forming a 5- or 6-membered heterocyclic ring other than a triazole ring; and each Z independently is $CF_3$, —OH, —Br, —Cl, —F, —CN, —$NO_2$, phosphonic acid, sulpho, optionally substituted phosphoramide, optionally substituted alkyl, optionally substituted alkenyl, optionally substituted alkynyl, optionally substituted aryl, optionally substituted aralkyl, —$SR^1$, —$SO_2R^1$, —$SO_2NR^2R^3$, —$SOR^1$, —$OR^1$, —$C(O)R^1$, —$C(O)OR^1$, —$C(O)NR^2R^3$, —$NR^2R^3$ or —$NHCOR^1$ wherein, $R^1$, $R^2$ and $R^3$ are each independently H, optionally substituted alkyl, optionally substituted alkenyl, optionally substituted alkynyl, optionally substituted aryl or optionally substituted aralkyl; or $R^2$ and $R^3$ together with the nitrogen to which they are attached form an optionally substituted 5- or 6-membered ring.

3. A compound according to claim 1 or 2 wherein each Z is, independently, a $C_{1-4}$-alkyl, carboxy or cyano group.

4. A compound according to claim 1 or 2 wherein X, Y and W are each selected from the group consisting of sulpho, sulphonamido, carboxy, halogen, nitro and cyano groups.

5. A compound according to claim 1 or 2 wherein M is nickel.

6. A compound according to claim 1 or 2 wherein X, Y and W are sulpho groups.

7. A compound according to claim 1 or 2 wherein A is an optionally substituted imidazole, pyrazole or pyridine group.

8. A metal chelate compound according to claim 1 of Formula (4a) or (4b) or a salt thereof:

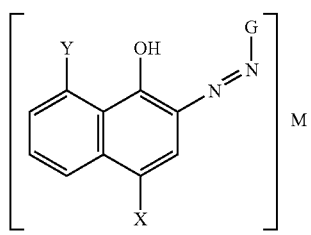

Formula (4a)

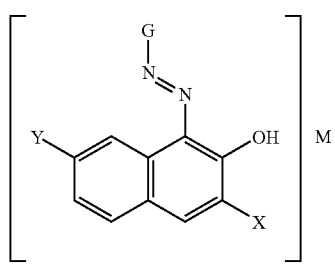

Formula (4b)

wherein:

G is an optionally substituted imidazole, pyrazole or pyridine group;

M is nickel, chelated to the group shown in square brackets; and

X and Y are selected from the group consisting of sulpho, sulphonamido, carboxy, halogen, nitro and cyano groups.

9. An ink comprising:
(a) a compound of the Formula (1) as defined in claim 1 or 2; and
(b) a liquid medium comprising a mixture of water and an organic solvent.

10. A process for printing an image on a substrate comprising applying thereto by means of an ink jet printer an ink containing a compound according to claim 1 or 2.

11. An ink jet printer cartridge comprising a chamber and ink, wherein the ink is present in the chamber and the ink contains a compound according to claim 1, 2 or 8.

12. An ink jet printer containing an ink jet printer cartridge, wherein the ink jet printer cartridge is as defined in claim 11.

13. A compound according to claim 3 wherein M is nickel.

14. An ink comprising:
(a) a compound of the Formula (4a) or (4b) as defined in claim 10; and
(b) a liquid medium comprising a mixture of water and an organic solvent.

* * * * *